US009451993B2

United States Patent
Jackson et al.

(10) Patent No.: US 9,451,993 B2
(45) Date of Patent: Sep. 27, 2016

(54) BI-RADIAL POP-ON CERVICAL BONE ANCHOR

(71) Applicant: Roger P. Jackson, Prairie Village, KS (US)

(72) Inventors: Roger P Jackson, Prairie Village, KS (US); James L Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 14/591,651

(22) Filed: Jan. 7, 2015

(65) Prior Publication Data

US 2015/0190176 A1    Jul. 9, 2015

Related U.S. Application Data

(60) Provisional application No. 61/925,420, filed on Jan. 9, 2014.

(51) Int. Cl.
*A61B 17/70*    (2006.01)
*A61B 17/86*    (2006.01)

(52) U.S. Cl.
CPC ......... *A61B 17/7037* (2013.01); *A61B 17/862* (2013.01); *A61B 17/7082* (2013.01)

(58) Field of Classification Search
CPC .......... A61B 17/7035; A61B 17/7037; A61B 17/7038; A61B 17/7046
See application file for complete search history.

(56) References Cited

U.S. PATENT DOCUMENTS

| | | |
|---|---|---|
| 154,864 A | 9/1874 | Harvey |
| 791,548 A | 6/1905 | Fischer |
| 1,300,275 A | 4/1919 | Johnson |
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |

(Continued)

FOREIGN PATENT DOCUMENTS

| | | |
|---|---|---|
| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001, pp. 1-8.
CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.

(Continued)

*Primary Examiner* — Eduardo C Robert
*Assistant Examiner* — Julianna N Harvey
(74) *Attorney, Agent, or Firm* — Polsinelli PC

(57) ABSTRACT

A cervical polyaxial bone anchor includes a longitudinal connecting member receiver structure and a cooperating shank. The shank has a body and an integral head with first and second spherical surfaces of different radii and a plurality of spaced curvate apertures for receiving portions of the longitudinal connecting member to result in a greater angle of inclination of the shank with respect to the receiver. The receiver has an upper channel and a lower cavity that further includes an expansion area and an operational seat for a split retainer ring that captures and fixes the shank head within the receiver.

13 Claims, 9 Drawing Sheets

(56) References Cited

U.S. PATENT DOCUMENTS

| | | |
|---|---|---|
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,323,326 A | 4/1982 | Okada et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Baker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |

(56) References Cited

U.S. PATENT DOCUMENTS

| | | |
|---|---|---|
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stuecker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schaefer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,989,254 A * | 11/1999 | Katz ............... A61B 17/7038 606/308 |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,139,549 A | 10/2000 | Keller |
| 6,143,032 A | 11/2000 | Schaefer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,371,957 B1 | 4/2002 | Amrein |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |

(56) References Cited

U.S. PATENT DOCUMENTS

| | | |
|---|---|---|
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,835,196 B2 | 12/2004 | Biedermann et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,179,261 B2 | 2/2007 | Sicvol et al. |
| 7,316,684 B1 | 1/2008 | Baccelli et al. |
| 7,672,394 B2 | 3/2010 | Molz, IV et al. |
| 7,686,833 B1 | 3/2010 | Muhanna et al. |
| 7,766,943 B1 | 8/2010 | Fallin et al. |
| 7,833,251 B1 | 11/2010 | Ahlgren et al. |
| 7,862,587 B2 | 1/2011 | Jackson |
| 7,947,065 B2 | 5/2011 | Hammill, Sr. et al. |
| 7,972,364 B2 | 7/2011 | Biedermann et al. |
| 8,043,340 B1 | 10/2011 | Law |
| 8,092,499 B1 | 1/2012 | Roth |
| 8,114,133 B2 | 2/2012 | Logan |
| 8,114,134 B2 | 2/2012 | Winslow et al. |
| 8,133,262 B2 | 3/2012 | Whipple |
| 8,167,914 B1 | 5/2012 | Hunt et al. |
| 8,197,517 B1 | 6/2012 | Lab et al. |
| 8,206,422 B2 | 6/2012 | Hestad et al. |
| 8,211,110 B1 | 7/2012 | Corin et al. |
| 8,236,035 B1 | 8/2012 | Bedor |
| 8,388,659 B1 | 3/2013 | Lab et al. |
| 8,394,133 B2 | 3/2013 | Jackson |
| 8,439,922 B1 | 5/2013 | Arnold et al. |
| 8,439,924 B1 | 5/2013 | McBride et al. |
| 8,444,681 B2 | 5/2013 | Jackson et al. |
| 8,470,009 B1 | 6/2013 | Rezach |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1* | 7/2002 | Martin ............... A61B 17/7037 606/278 |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiancomo |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149430 A1 | 8/2003 | Ferrante et al. |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |

(56) References Cited

U.S. PATENT DOCUMENTS

| | | |
|---|---|---|
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039383 A1 | 2/2004 | Jackson |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127897 A1 | 7/2004 | Freid et al. |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0021036 A1 | 1/2005 | Whitmore et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Iott et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |

(56) References Cited

U.S. PATENT DOCUMENTS

| | | |
|---|---|---|
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149235 A1 | 7/2006 | Jackson |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann et al. |
| 2006/0184180 A1 | 8/2006 | Augostino et al. |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm |
| 2006/0229614 A1 | 10/2006 | Foley et al. |
| 2006/0229615 A1 | 10/2006 | Abdou |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247635 A1 | 11/2006 | Gordon et al. |
| 2006/0247658 A1 | 11/2006 | Pond et al. |
| 2006/0247779 A1 | 11/2006 | Gordon et al. |
| 2006/0260483 A1 | 11/2006 | Hartmann et al. |

(56) References Cited

U.S. PATENT DOCUMENTS

| | | |
|---|---|---|
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |
| 2007/0073290 A1 | 3/2007 | Boehm |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0129729 A1 | 6/2007 | Petit et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0219554 A1 | 9/2007 | Landry et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045963 A1* | 2/2008 | Abdou ............... A61B 17/7032 606/86 A |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |

(56) References Cited

U.S. PATENT DOCUMENTS

| | | |
|---|---|---|
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012562 A1 | 1/2009 | Hestad et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |

(56) References Cited

U.S. PATENT DOCUMENTS

| | | |
|---|---|---|
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0228292 A1 | 9/2010 | Arnold et al. |
| 2010/0234902 A1 | 9/2010 | Biedermann et al. |
| 2010/0249843 A1 | 9/2010 | Wegrzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |

(56) References Cited

U.S. PATENT DOCUMENTS

| | | |
|---|---|---|
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson et al. |
| 2012/0046699 A1 | 2/2012 | Jones et al. |
| 2012/0053636 A1 | 3/2012 | Schmocker |
| 2012/0071928 A1 | 3/2012 | Jackson |
| 2012/0078307 A1 | 3/2012 | Nihalani |
| 2012/0197314 A1 | 8/2012 | Farris |
| 2012/0232598 A1 | 9/2012 | Hestad et al. |
| 2012/0310284 A1 | 12/2012 | Gerchow |
| 2013/0103097 A1 | 4/2013 | May et al. |
| 2013/0150852 A1 | 6/2013 | Shluzas et al. |

FOREIGN PATENT DOCUMENTS

| | | |
|---|---|---|
| DE | 3630863 | 3/1988 |
| DE | G9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846223 | 4/2004 |
| FR | 2857850 | 4/2004 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |

(56) References Cited

FOREIGN PATENT DOCUMENTS

| | | |
|---|---|---|
| WO | 03037199 | 5/2003 |
| WO | 03047442 | 6/2003 |
| WO | 03068083 | 8/2003 |
| WO | 03068088 | 8/2003 |
| WO | 03084415 | 10/2003 |
| WO | 03094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2007089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008006098 | 1/2008 |
| WO | 2008008511 | 1/2008 |
| WO | 2008013892 | 1/2008 |
| WO | 2008146032 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.

* cited by examiner

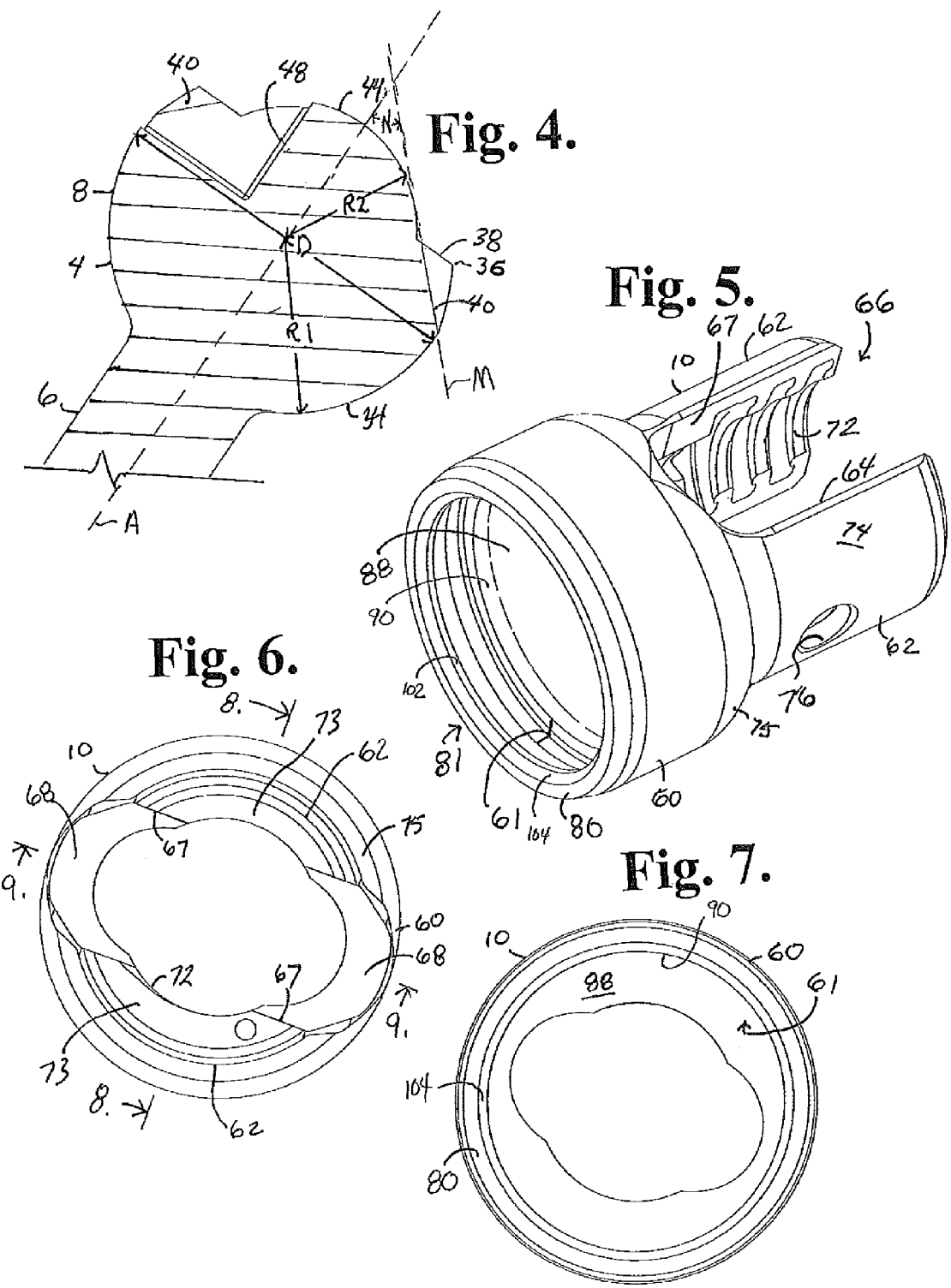

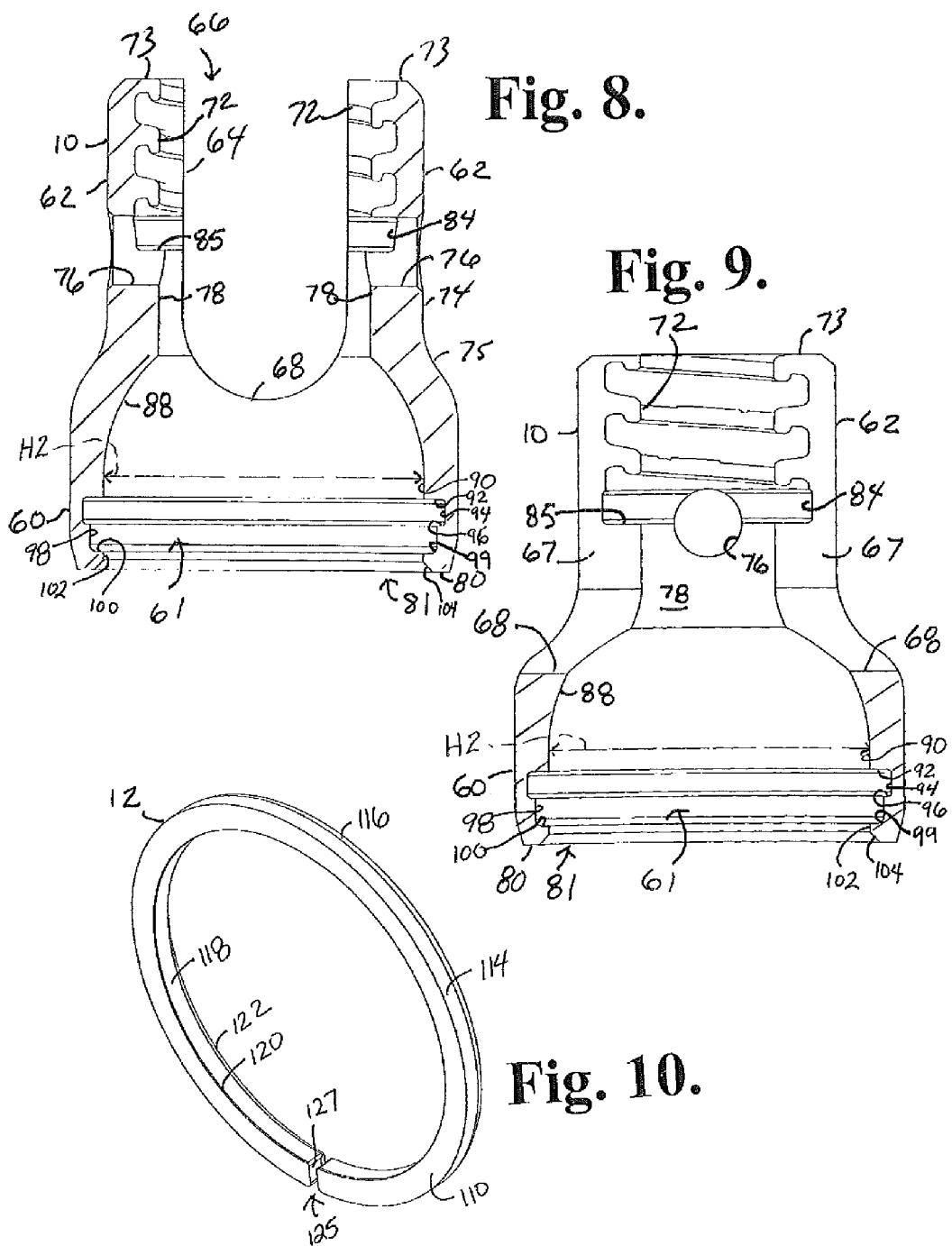

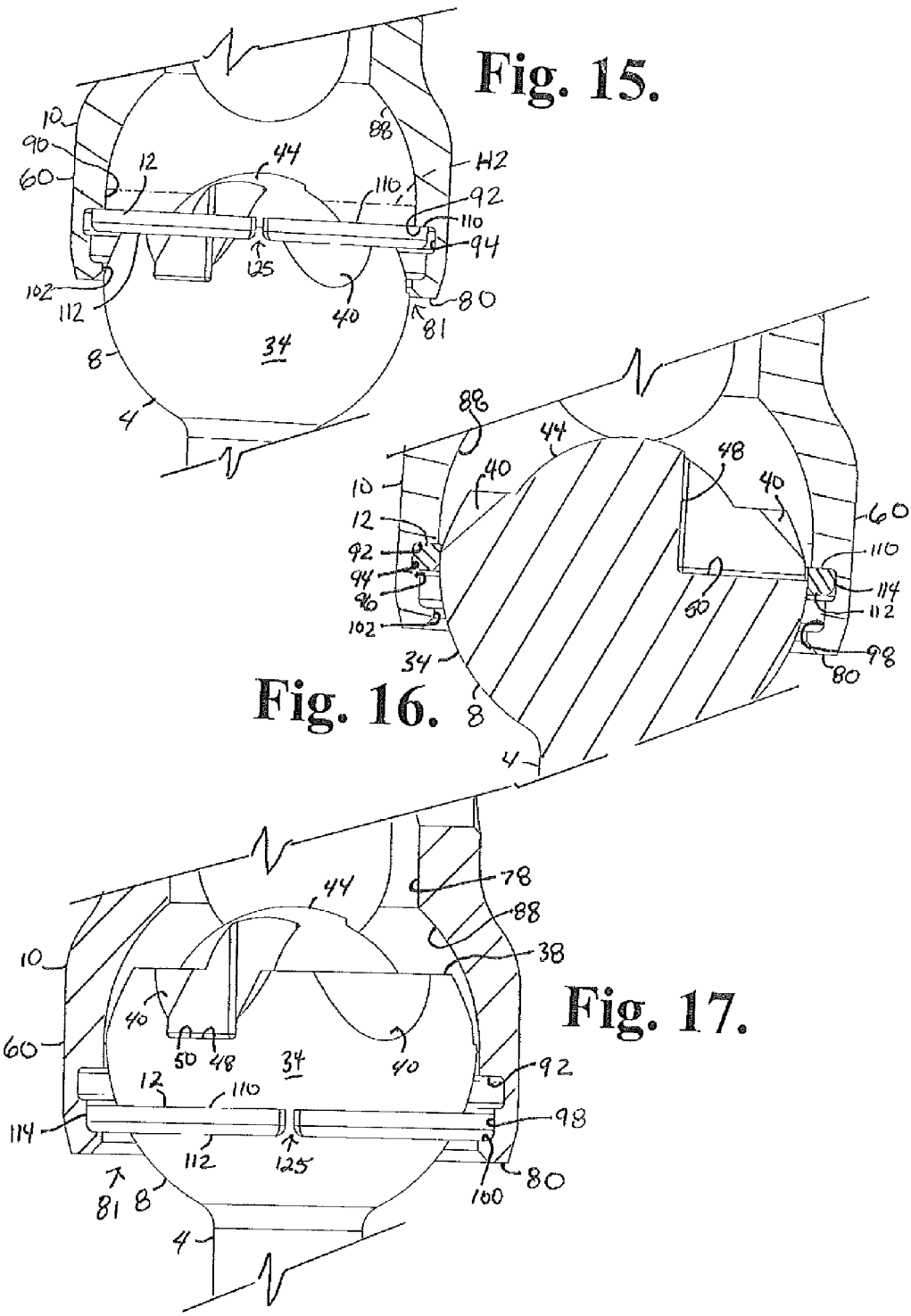

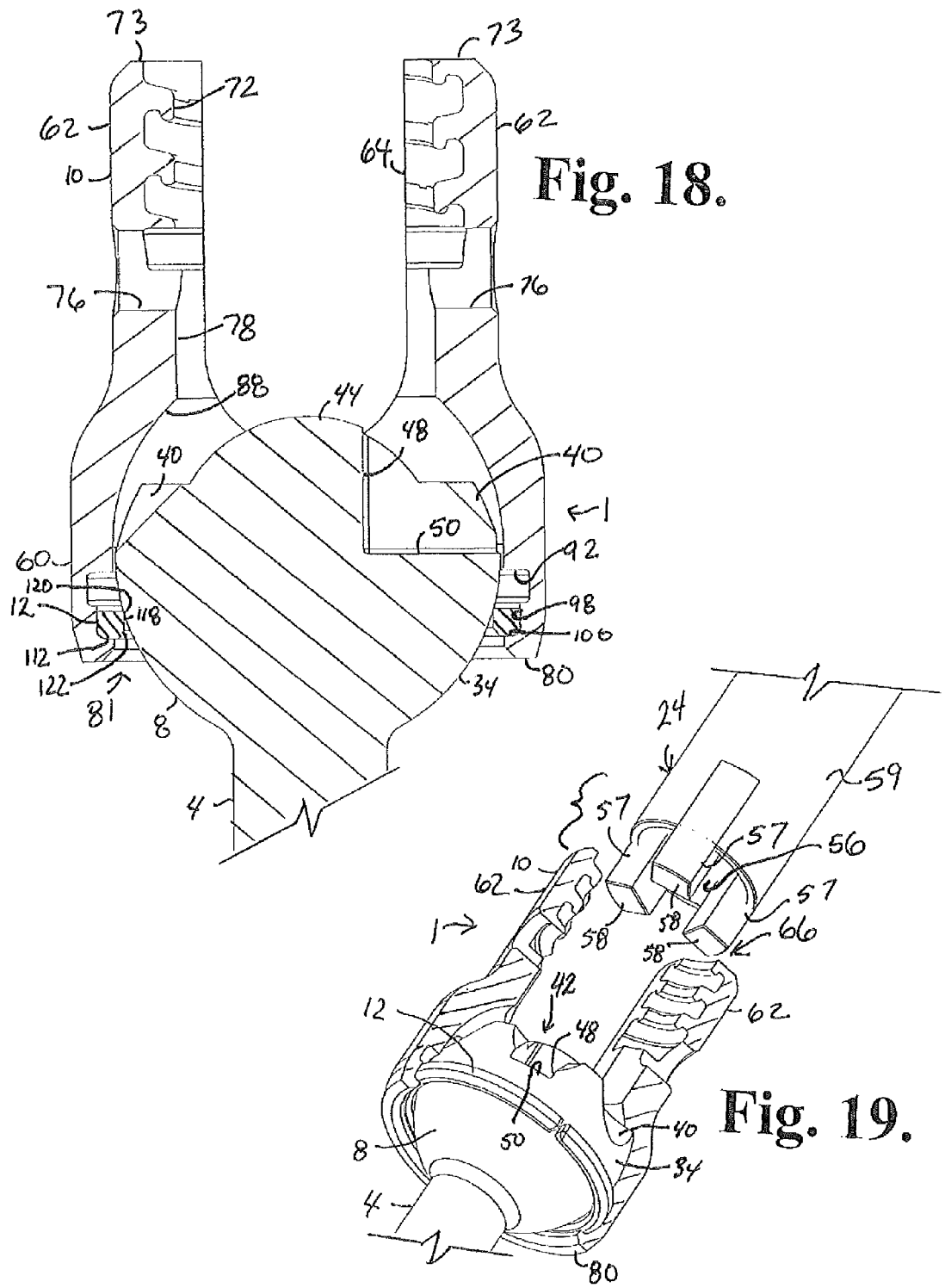

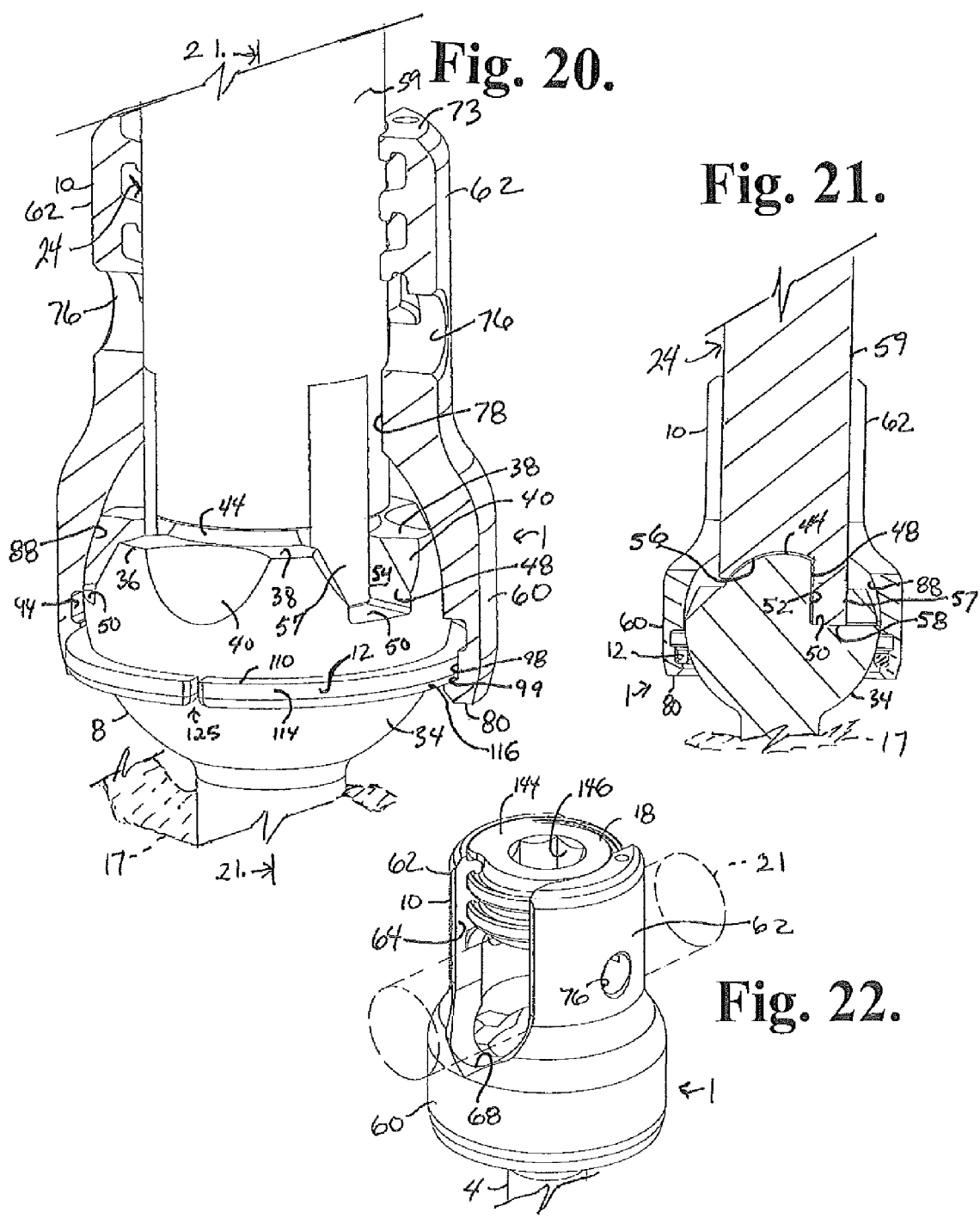

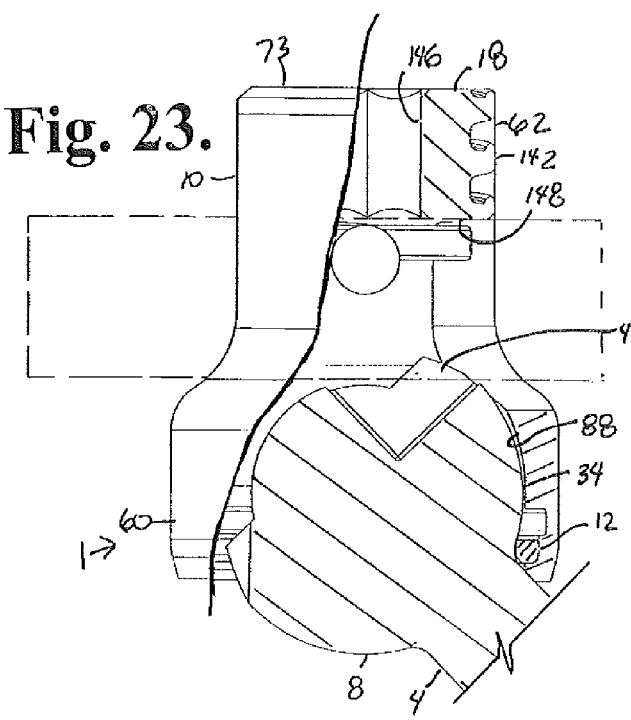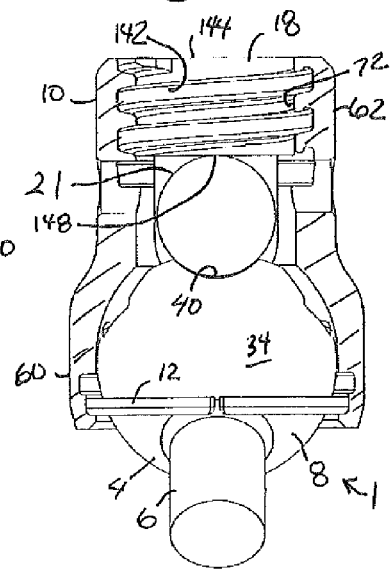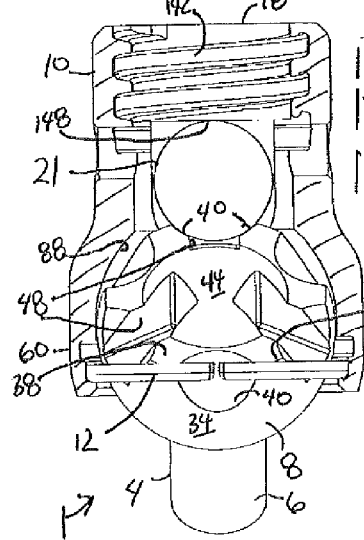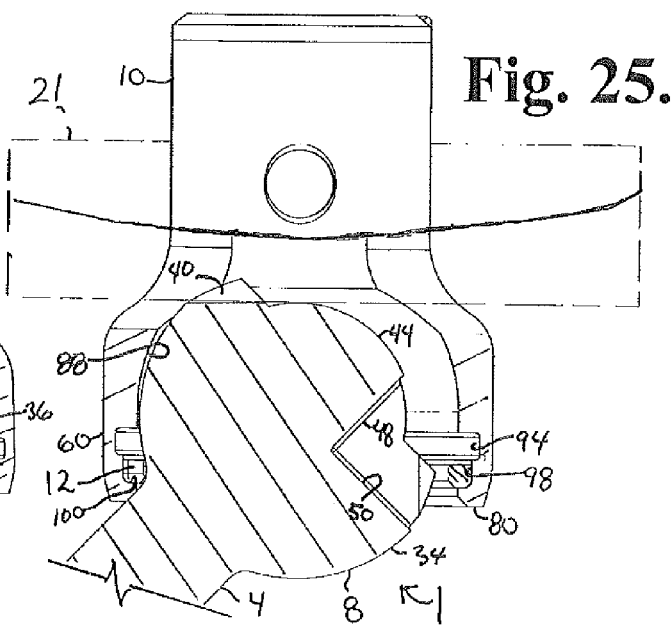

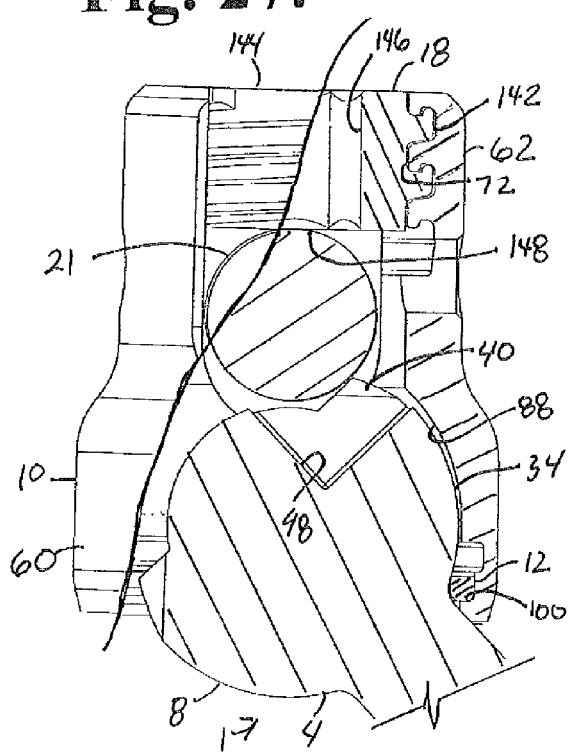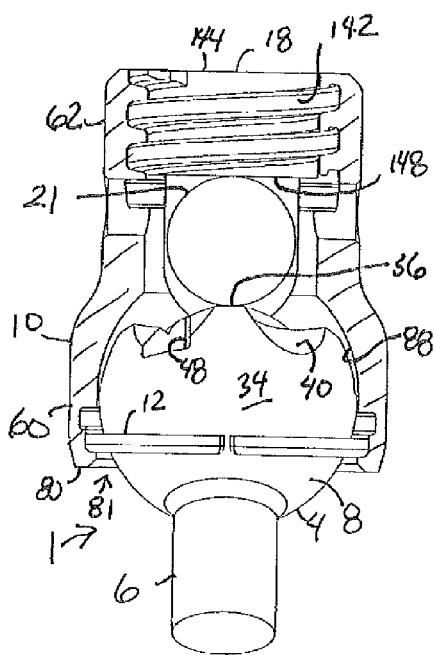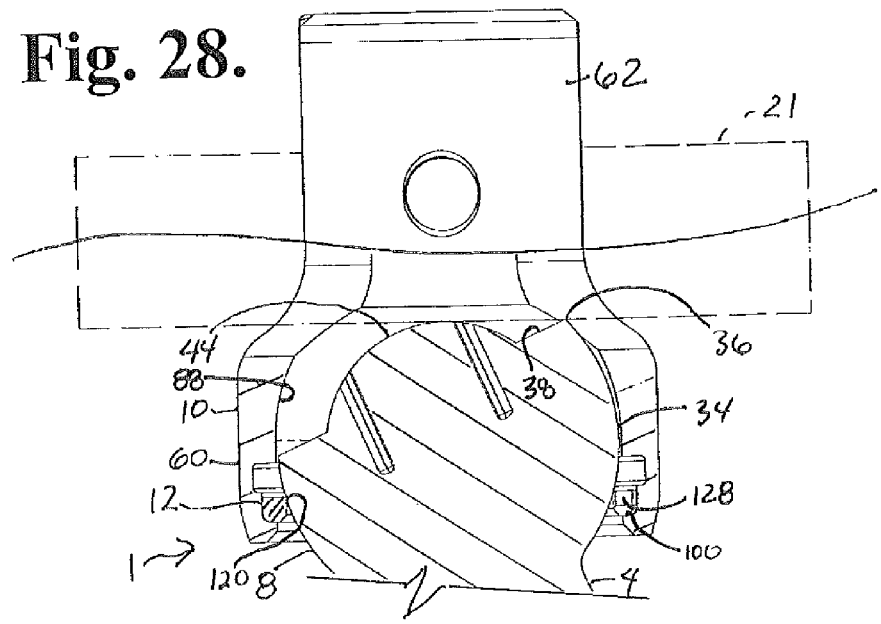

BI-RADIAL POP-ON CERVICAL BONE ANCHOR

CROSS-REFERENCE TO RELATED APPLICATIONS

This application claims the benefit of U.S. Provisional Ser. No. 61/925,420, filed Jan. 9, 2014, which is incorporated by reference herein.

BACKGROUND OF THE INVENTION

The present invention is directed to polyaxial bone anchors for use in bone surgery, particularly spinal surgery and particularly to such bone anchors with retainers for capturing and retaining a bone screw shank head in the receiver member assembly and later fixing the bone screw shank with respect to the receiver assembly.

Bone screws are utilized in many types of spinal surgery in order to secure various implants to vertebrae along the spinal column for the purpose of stabilizing and/or adjusting spinal alignment. When vertebrae of the cervical spine are involved, the connecting structure or structures commonly include a plate and cooperating relatively smaller screws. When the connector is in the form of a rod, both closed-ended and open-ended bone screws are known with open-ended screws being particularly well suited for connections to rods and connector arms because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or rod receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult, but desirable in other situations.

SUMMARY OF THE INVENTION

An embodiment of the present invention is a polyaxial spinal bone screw assembly for receiving and fixing placement of a longitudinal connecting member such as a rod. The assembly includes a bone screw shank having a body for insertion into bone integral with an upper portion or head. The shank head includes a top convex partially spherical first surface having a first radius and a lower convex partially spherically shaped surface having a second radius. A third annular surface extends outwardly from the first surface and terminates at the second surface at a spheric perimeter or edge. At least one and up to a plurality of spaced concave surface features are formed through the edge and thus into the annular and lower spherical surfaces. A rod or other longitudinal connector receiver structure has a pair of arms forming a channel as well as base that defines a cavity. The cavity is sized to allow for pivotal movement of the shank first and second surfaces there within. A lower opening communicates with the cavity and an exterior of the receiver opposite the pair of arms. The cavity communicates with the channel. The receiver cavity is further defined by a lower seat and an expansion area located above the lower seat. The bone screw head is uploaded and received in the cavity through the lower opening. The assembly further includes an open and resilient ring-like retainer receivable in the cavity and outwardly biased against the receiver in fixed relation thereto at the receiver seat when the shank head is captured in the receiver and fixed against the retainer by a downward force placed directly on the head by a rod or other longitudinal connecting member so as to fix or lock an angular position of the receiver relative to the shank. The retainer is expandable about the shank head at the receiver cavity expansion area during uploading of the shank head through the receiver lower opening. Prior to locking, the shank head is in sliding, pivotable relation with the retainer and the retainer is rotatable with respect to the receiver. Also, while still in an unlocked position a portion of the rod may be received in an area defined by one of the shank concave surface features to provide an increased angle of articulation between the shank and the receiver. Thereafter, another portion of the rod may then be fixed into locking engagement with the shank first convex surface.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is a cross-sectional view taken along the line 4-4 of FIG. 3.

FIG. 5 is an enlarged perspective view of the receiver of FIG. 1.

FIG. 6 is a top plan view of the receiver of FIG. 5.

FIG. 7 is a bottom plan view of the receiver of FIG. 5.

FIG. 8 is a cross-sectional view taken along the line 8-8 of FIG. 6.

FIG. 9 is a cross-sectional view taken along the line 9-9 of FIG. 6.

FIG. 10 is an enlarged perspective view of the open retainer of FIG. 1.

FIG. 15 is an enlarged and partial front elevational view with portions broken away of the receiver, retainer and shank of FIG. 14 and further showing the shank in an early stage of assembly with the retainer wherein the retainer is pushed upwardly against an inner surface of the receiver.

FIG. 16 is an enlarged and partial front elevational view with portions broken away, similar to FIG. 15, showing a head of the shank in a subsequent stage of assembly with the retainer, pressing the retainer outwardly to a configuration of maximum expansion against the receiver.

FIG. 17 is a partial front elevational view with portions broken away, similar to FIG. 16, showing the head of the shank pressed through the retainer and the retainer resiliently returned to a neutral or near neutral configuration.

FIG. 18 is a partial front elevational view with portions broken away, similar to FIG. 17, showing the shank head lowered to a seated position on the retainer.

FIG. 19 is a reduced and partial perspective view with portions broken away of the assembly as shown in FIG. 18 and further showing a shank driver tool, also in partial perspective view.

FIG. 20 is an enlarged and partial perspective view with portions broken away of the assembly of FIG. 19, showing the driver engaged with the shank to drive the shank into a vertebra, shown in a partial and partially schematic view.

FIG. 21 is a reduced and partial cross-sectional view taken along the line 21-21 of FIG. 20.

FIG. 22 is a reduced and partial perspective view of the assembly of FIG. 20 further shown assembled with the rod and closure of FIG. 1, also in perspective view, the rod in phantom to show details of the assembly.

FIG. 23 is an enlarged and partial side elevational view with portions broken away of the assembly of FIG. 22, but with the shank pivoted to a forty-four degree angle with respect to the receiver in the sagittal plane with the shank directed caudally, the rod in phantom to show details of the assembly.

FIG. 24 is a reduced and partial rear elevational view of the assembly of FIG. 23 with portions of the receiver broken away to show details of the assembly.

FIG. 25 is an enlarged and partial side elevational view with portions broken away of the assembly of FIG. 22, but with the shank pivoted to a forty-four degree angle with respect to the receiver in the sagittal plane with the shank pivoted in a cephalic direction, the rod in phantom to show details of the assembly.

FIG. 26 is a reduced and partial rear elevational view of the assembly of FIG. 25 with portions of the receiver broken away to show details of the assembly.

FIG. 27 is an enlarged and partial front elevational view with portions broken away of the assembly of FIG. 22 but with the shank pivoted to a forty-four degree angle with respect to the receiver in the transverse plane.

FIG. 28 is an enlarged and partial side elevational view with portions broken away of the assembly of FIG. 22 but with the shank rotated slightly and then pivoted to a twenty-four degree angle with respect to the receiver in the sagittal plane, the rod in phantom to show details of the assembly.

FIG. 29 is a reduced and partial rear elevational view of the assembly of FIG. 28 with portions of the receiver broken away to show the detail of the assembly.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
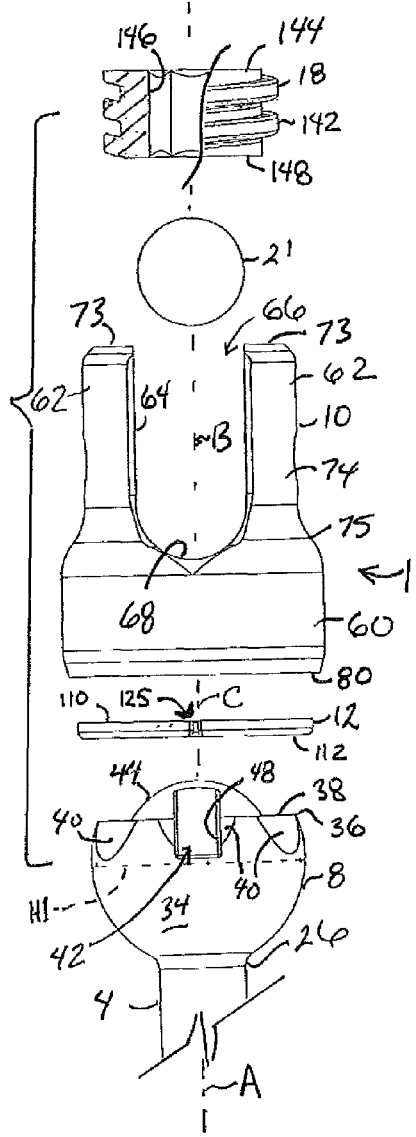
FIG. 1 is an exploded and partial front elevational view of a polyaxial bone screw assembly according to an embodiment of the present invention including a shank, an open retainer and a receiver and further showing a cooperating rod and closure top shown with portions broken away to show the detail thereof.

With reference to FIG. 1, the reference number 1 generally represents a polyaxial bone screw apparatus or assembly according to an embodiment of the present invention that includes a shank 4 that further includes a body 6 integral with an upwardly extending upper portion or head-like capture structure 8; a receiver 10; and an open ring retainer structure 12. The receiver 10 and retainer 12 are initially assembled by the vendor and may be further assembled with the shank 4 either by the vendor or by a user prior to or after implantation of the shank body 6 into a vertebra 17, as will be described in greater detail below. Thus, when desired, the shank 4 may be implanted into a vertebra first, followed by assembly with the other components. Even though such a procedure might not at first blush appear desirable on the smaller, more fragile cervical vertebrae, due to the small size of the assembly 1 and that only between about forty and about fifty inch pounds of torque is required for attaching a closure structure 18 to the receiver 10 to capture and fix a longitudinal connecting member, such as a rod 21 to the assembly 1, the initial posting or implantation of the shank 4 followed by a push- or snap-on assembly with the receiver 10 is acceptable and may be a desired procedure in some circumstances. FIG. 1 further shows such closure structure 18 for capturing the longitudinal connecting member, for example, shown as a 3.5 millimeter diameter rod 21 which in turn engages the shank head 8 that in turn presses into fixed frictional contact with the retainer 12, so as to capture, and fix the longitudinal connecting member 21 within the receiver 10 and thus fix the member 21 relative to the vertebra 17.

The illustrated rod 21 is hard, stiff, non-elastic and cylindrical; however, it is foreseen that in other embodiments, the rod 21 may be elastic, deformable and/or of a different cross-sectional geometry. Although a 3.5 mm diameter rod is shown, the rod for use with the cervical assembly 1 could be smaller or bigger, with diameter measurements of 3.0 mm, 3.75 mm and 4.0 mm also being common (and with the receiver 10 being sized accordingly to cooperate with such diameter size). In some embodiments, the bone screw assembly 1 may also cooperate with soft connecting systems, such as spinal connectors having rigid sleeves for placement within bone screw receivers in lieu of a rod, such sleeves including through bores for receiving a tensioned cord, for example.

As will be described in greater detail below the receiver 10 and the head 8 of the shank 4 cooperate in such a manner that the receiver 10 and the shank 4 can be secured at a plurality of different angles, articulations and rotational alignments relative to one another and within a selected range of angles both from side to side and from front to rear, to enable flexible or articulated engagement of the receiver 10 with the shank 4 until both are locked or fixed relative to each other near the end of an implantation procedure. The drawings at FIGS. 19-21 also illustrate a driver, generally 24 for use with the assembly 1 as will be described in greater detail below.

The shank 4, best illustrated in FIGS. 1-4, is elongate, the shank body 6 being only partially shown in the drawing figures. The body 6 is elongate and further includes one or more helically wound threads for bone engagement that are known in the art of pedicle screws, in particular smaller screws sized and shaped for use on the cervical spine. An example of a larger pedicle screw shank for use with some embodiments of the invention is illustrated, for example, in U.S. Pat. No. 6,726,689, which is also incorporated herein by reference to provide examples of flange form guide and advancement structures for use with receivers 10 and closures 18 of embodiments of the invention. During use, the body 6 utilizing the thread or threads (not shown) for gripping and advancement is implanted into the vertebra 17 (e.g., see FIG. 20) leading with a tip of the shank 6 and driven down into the vertebra with an installation or driving tool, such as the tool 24, so as to be implanted in the vertebra to a location at or near a neck thereof, as more fully described in the paragraphs below. The shank 4 has an elongate axis of rotation generally identified by the reference letter A.

A neck 26 extends axially upward from the shank body 6. The neck 26 may be of the same or of a slightly reduced radius as compared to an adjacent upper end or top of the body 6 where the thread or threads terminate. Extending axially upwardly and radially outwardly from the neck 26 is the shank upper portion or head 8 that provides a connective or capture apparatus disposed at a distance from the threaded portion of the shank 6 and thus at a distance from the vertebra 17 when the body 6 is implanted in such vertebra.

The shank upper portion or head 8 is configured for engagement between the portion 8 and the retainer 12 (ultimately an operative fixed, frictional engagement) and a pivotable connection between the shank 4 and the receiver 10 prior to fixing of the shank 4 in a desired position with respect to the receiver 10. The shank head or upper portion 8 has a first outer, convex and substantially spherical surface 34 that extends outwardly and upwardly from the neck 26. A dotted line H1 in FIG. 1 indicates a hemisphere of the lower spherical surface 34 that has a maximum or major diameter D at such hemisphere H1 as shown in FIG. 4. A radius R1 shown in FIG. 4 is the radius of the surface 34 at the major diameter D so D=2R1. The spherical surface 34 radius R1 is configured for frictional sliding and then ultimate fixed cooperation with the retainer 12 as will be discussed more fully in the paragraphs below. The shank spherical surface 34 is locked into place at the retainer 12 and not by inner surfaces defining the receiver 10 cavity, the shank head 8 being held in spaced relation with the receiver 10 by the retainer 12. The spherical surface 34 shown in the present embodiment is substantially smooth, but in some embodiments may include a roughening or other surface treatment to enhance frictional engagement with the retainer 12. The surface 34 terminates at a circular spheric edge 36 that extends around a perimeter of the surface 34 and intersects with and also partially defines an outer perimeter of a discontinuous annular surface 38 located spaced from and above the hemisphere H1. The annular surface 38 and the adjacent spherical surface have formed thereon a plurality of uniformly formed and spaced curvate concave surfaces 40 as well as a multi-pronged drive receiving feature, generally 42, that will be described in greater detail below. The surface 38 is substantially planar and disposed perpendicular to the axis A. The surface 38 extends radially inwardly of the spherical surface 34 starting at the spheric edge 39 and terminates at a second convex and substantially spherical upper surface or dome 44. The dome 44 has a radius R2 that is smaller than the radius R1 of the spherical surface 34. Both the radii R1 and R1 are measured from the shank central axis A. The domed surface 44 radius is configured such that the rod 21 directly engages and is fixable against the surface 44 at any and all operative angular configurations of the shank 4 with respect to the receiver 10. The illustrated domed surface 44 is smooth. However, the surface 44 may include ridges, a roughening or other surface treatment to provide enhanced frictional contact between the rod 21 and the surface 44.

Figure 2:
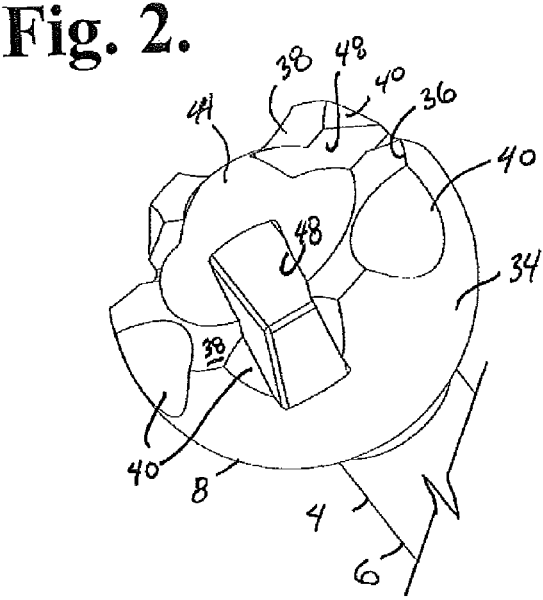
FIG. 2 is an enlarged and partial perspective view of the shank of FIG. 1.
Figure 3:
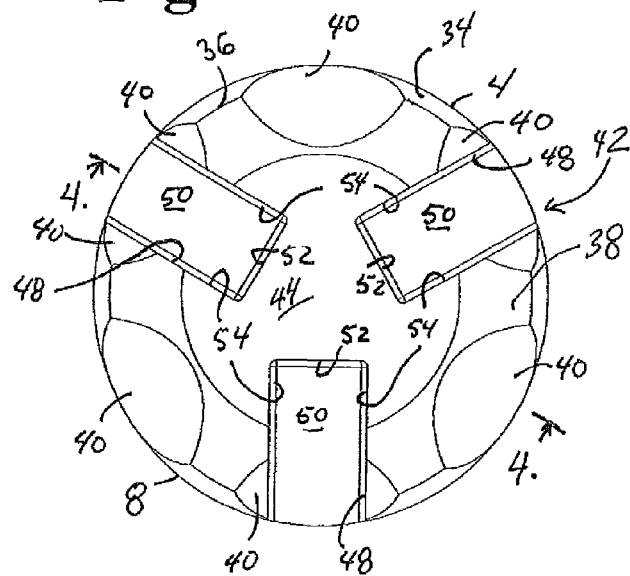
FIG. 3 is an enlarged top plan view of the shank of FIG. 2.
Figure 11:
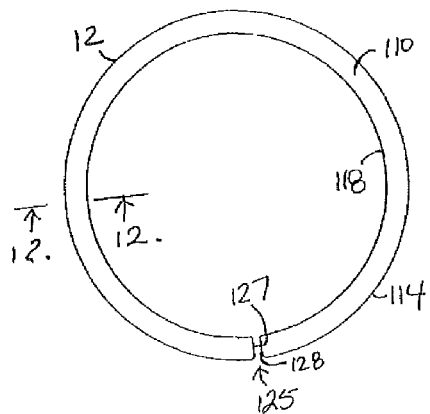
FIG. 11 is a reduced top plan view of the retainer of FIG. 10.
Figure 12:
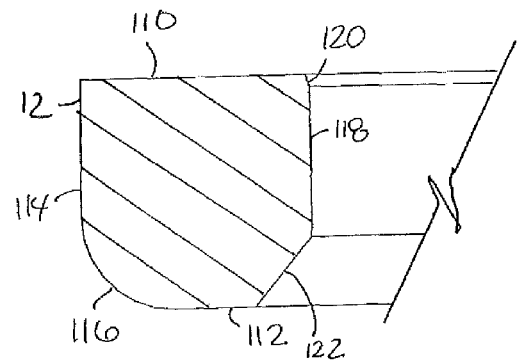
FIG. 12 is an enlarged and partial cross-sectional view taken along the line 12-12 of FIG. 11.

With further reference to FIGS. 2 to 4, there are six substantially evenly spaced apertures or cut-out surfaces 40 of identical or substantially similar size and shape that are formed into the shank head surfaces 34 and 38 and thus into the perimetric spheric edge 36. Thus, the loading edge 36 that is substantially circular and located above the hemisphere H1 is made discontinuous by the six arcuate surface formations 40. Three of the surface features 40 further include a drive slot 48 of the drive feature 42 as will be described in greater detail below. Each of the surfaces 40 is sized and shaped so as to provide a partially curved or partially cylindrical seat to receive a portion of the rod 21 as shown, for example in FIGS. 23-25 to allow for an increased or maximum angle of inclination of the shank 4 with respect to the receiver 10, which in the illustrated embodiment is approximately forty-four degrees. Thus, as shown in FIG. 4 each surface 40 is configured to receive the rod 21 along or near a line M that forms an angle N with respect to the shank axis A that in the illustrated embodiment is approximately forty-four degrees. It is foreseen that in other embodiments of the invention the angle N may be greater or smaller. However, for angles greater than forty-four degrees, the cylindrical or curved cut-out area provided by each surface portion 42 would also be wider which might eliminate or substantially reduce the size of the annular surface 38 and thus the loading edge 36 of the spherical surface 34 located between each of the curved cut-outs 40. Such a decrease of the loading edge 36 located between each surface feature 40 would not be desirable as the spheric loading edge 36 and the spherical loading surfaces 34 located adjacent and below the edge 36 are sized for securely retaining the head 8 within the ring 12 and thus prohibiting pull-out of the shank head 8 from the receiver 10 when the shank 4 is pivoted at higher angles such as the forty-four degree angle shown in FIG. 23, for example. It is noted that in other embodiments more or fewer formations 40 may be used. The illustrated combination of spaced concave surface formations 40, each with adjacent spherical surface portions 34 that terminate at the spheric edge 36, advantageously result in the bi-radial shank 4 that may be pivoted to up to about 44 degrees with respect to a cooperating rod 21 at a plurality of locations on the shank head 8 and thus at a plurality of positions with respect to the receiver 10 while keeping such shank head 8 securely within the receiver 10. It is noted that the term bi-radial in this application may apply to two different aspects of the shank head 8. In a first aspect, the shank head 8 has a first spherical surface 34 with a first radius R1 and a second spherical surface 44 or dome that engages the rod that has a second, smaller radius R1. In a second aspect, the illustrated shank 4 may be described as having a bi-radial symmetry because the concave cuts or surface formations 40 are located opposite one another on either side of the axis A and one surface portion 34 having the upper support edge 36 is located adjacent to and between each formation 40.

As best shown in FIG. 3, the internal drive feature 42 that includes the three drive slots or grooves 48 is formed in an upper portion of the head 8, specifically in the domed surface 44, the annular surface 38 and three of the concave features 40. Each drive slot 48 includes a counter sunk substantially planar base 50 an inner planar wall 52 and planar opposed side walls 54. Each slot 48 is open at the head spherical surface 34 and extends radially inwardly toward the axis A. Each slot 48 extends into the convex domed surface 44, but the slots 48 do not intersect or otherwise communicate with one another at the surface 44, leaving a substantial portion of the surface 44 located on and near the axis A intact for providing adequate surface area for frictional engagement between the spherical surface 44 and the rod 21 or other longitudinal connecting member. With reference to FIGS. 19-21, the driver 24 is equipped with an inner concave spherical surface 56 and three outer, evenly spaced prongs 57 sized and shaped for insertion over the domed surface 44, with the three prongs brining received by the three radially extending slots 48 of the feature 42. Each prong 57 has a substantially planar end surface 58 sized and shaped for frictional engagement with one of the drive slot base surfaces 50, the prongs 57 being evenly spaced and illustrated as being fixed to (or may be integral with) a substantially cylindrical elongate shaft 59. The shaft 59 may be part of a larger holding and driving tool system known in the art. The three slots 48 of the drive feature 42 are substantially uniform and are sized and spaced such that the slots 48 run centrally through every other curvate surface feature 40 with a portion of the surface feature 40 being cut by the slot 48 remaining on either side of each slot 48. Thus the rod 21 or other longitudinal connecting member may only engage the surface feature 40 on either side of the slot 48 and cannot enter more deeply into a space defined by the drive slot 48 (as shown in FIG. 26, for example). It is foreseen that in other embodiments, the three-drive slot drive feature 42 on the shank head 8 may take other tool-engaging forms and may include, for example, fewer or more apertures or slots of various shapes, such as a pair of spaced apart apertures, for example. The illustrated seat or base surface 50 of each drive slot 48 of the drive feature 42 is disposed substantially perpendicular to the axis A with the drive feature 42 being coaxial with the axis A. The illustrated drive seats 50 further include beveled or stepped surfaces that may further enhance gripping with the driving tool 24 at the prongs 57. As will be described in greater detail below, in operation, the driving tool prongs 57 are received in the internal drive slots 48, being seated at the base surfaces 50 and engaging the side walls 54 for rotating and driving the shank body 6 into the vertebra 17, either before the shank 4 is attached to the receiver 10 or after the shank 4 is attached to the receiver 10, with the shank body 6 being driven into the vertebra 17 with the driving tool extending into the receiver 10 as shown in FIGS. 20 and 21, for example.

The shank 4 shown in the drawings is solid, but in some embodiments may be cannulated, having a small central bore extending an entire length of the shank 4 along the axis A. Such a bore is typically defined by an inner cylindrical wall of the shank 4 having a circular opening at the shank driving tip and an upper opening at the domed top 44. Such a bore is typically coaxial with the threaded body 6 and the upper portion 8. Such a bore provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 5-9, the receiver 10 has a generally U-shaped appearance with various discontinuous and continuous curved inner and outer profiles. The receiver 10 has a central axis of rotation B that is shown in FIG. 1 as being aligned with and the same as the axis of rotation A of the shank 4, such orientation being desirable during assembly of the receiver 10, retainer 12 with the shank 4. After the receiver 10 is pivotally attached to the shank 4, the axis B is typically disposed at an angle with respect to the axis A, as shown, for example, in FIGS. 23-28.

The receiver 10 includes a base or lower body portion 60 that is illustrated as having a cylindrical outer surface, that in some embodiments may include other outer surface geometries, including curved, frusto-conical and partially planar. The base 60 defines a bore or inner cavity, generally 61, the base 60 being integral with a pair of opposed upstanding arms 62 forming a cradle and defining a channel 64 between the arms 62 with an upper opening, generally 66. The channel 64 is further defined by partially planar interior arm surfaces 67 that transition to a U-shaped lower saddle or seat 68, the channel 64 having a width for operably snugly receiving the rod 21 or portion of another longitudinal connector between the arms 62; the channel 64 communicating with the base cavity 61.

Each of the arm interior surfaces 67 have formed or machined therein various inner cylindrical profiles, an upper one of which is a partial helically wound guide and advancement structure 72 located adjacent a top surface or rim 73 of each of the arms 62. In the illustrated embodiment, the guide and advancement structure 72 is a partial helically wound interlocking flange form configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms could have break-off extensions in some embodiments.

Outer surfaces 74 of each arm 62 are substantially cylindrical and further include frusto-conical or curved transition surfaces 75 that extend radially outwardly to transition to the substantially cylindrical base 60. A pair of opposed substantially cylindrical through bores 76 are located centrally in the arms 72, each bore formed on one of the outer surfaces 74 and extending through the arm inner surface at a cylindrical portion 78 thereof located beneath the guide and advancement structure 72. The opposed bores 76 may be used with tools for holding the receiver 10 during assembly with the other components (12 and 4) of the bone anchor assembly 1 and during implantation and manipulation of the assembly 1 during surgery, for example. It is foreseen that other tool receiving grooves, depressions or apertures may be configured in a variety of shapes and sizes and be disposed at other locations on the receiver arms 62 and receiver base 60. Below the u-shaped seat 68, the substantially cylindrical base 60 eventually tapers inwardly slightly and then terminates at a substantially planar bottom surface 80 that partially defines an opening, generally 81 into the receiver cavity 61.

Returning to the interior surfaces 67 of the receiver arms 62, located below each guide and advancement structure 72 is a discontinuous cylindrical surface 84 partially defining a run-out feature for the guide and advancement structure 72. The cylindrical surface 84 has a diameter equal to or slightly greater than a greater diameter of the guide and advancement structure 72. Moving downwardly in a direction toward the base 60, adjacent the cylindrical surface 94 of each arm is a run-out seat or surface 85 that extends inwardly toward the axis B and is substantially perpendicular to the axis B. In other embodiments, the surface 85 may gently slope downwardly toward the axis B. Adjacent to and located below the surface 85 are planar inner arm surface portions as well as the centrally located cylindrical surface portion 78 through which the bore 76 extends. Portions of each bore 76 also extend through the cylindrical surface 84 and the run-out seat 85. The surface 78 terminates at a concave substantially spherical surface 88 that extends downwardly along each inner arm 67 and also between and below the curved surfaces defining the u-shaped channel seat 68, the surface 88 thus defining an upper portion of the base cavity 61 where the cavity 61 communicates with the u-shaped channel 64. The partially spherical or radiused surface 88 terminates at a largest diameter or hemisphere H2 thereof (shown in phantom) with H2 being slightly larger and thus slightly greater in diameter than the diameter D of the shank head surface 34 having the hemisphere H1. At the hemisphere H2, the surface 88 transitions into a cylindrical surface 90. The surface 90 terminates at an overhang or ceiling surface 92. The surface 92 is annular and perpendicular to the axis B. The surface 92 extends radially outwardly to a cylindrical surface 94 that terminates at a lower annular seat or ledge 96. The surfaces 92, 94 and 96 define an expansion chamber for the retainer 12 as will be described in greater detail below. The surface 92 is perpendicular to the cylindrical surface 94. The surface 96 curves or slopes slightly downwardly and inwardly toward and to another cylindrical surface and 98 that transitions to an annular surface or operation seat 100 for the retainer 12. The illustrated surfaces 98 and 100 are connected by one or more curved or sloping surfaces 99, the surfaces 98, 99 and 100 operationally capturing and seating the retainer 12 against the receiver 10 as will be described in greater detail below; the retainer 12 in turn capturing the shank 8 within the receiver cavity 61. The surface 100 terminates at another cylindrical surface 102. The cylindrical surface 94 has a diameter greater than a diameter of the cylindrical surface 98 that in turn has a diameter greater than a diameter of the cylindrical surface 102. The diameter of the surface 102 is substantially the same or slightly greater than the diameter measured at the hemisphere H2 of the radiused surface 88 that is also the diameter of the cylindrical surface 90. Thus, the surface 102 is sized to receive the shank head 8 at the greatest diameter D thereof. The cylindrical surface 102 terminates at an outwardly flaring frusto-conical surface 104 that terminates at the base surface 80, the surfaces 102, 104 and 80 forming the lower opening 81 of the receiver cavity 61.

Figure 13:
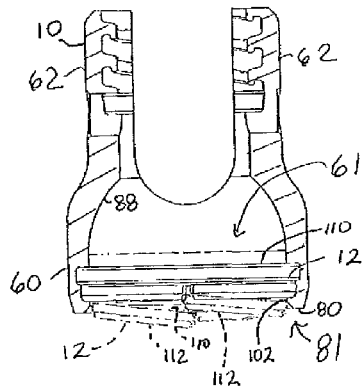
FIG. 13 is a reduced front elevational view of the receiver and retainer of FIG. 1 shown in a stage of assembly, the retainer shown in phantom in an earlier stage of assembly and the receiver shown with portions broken away to show the detail thereof.

With particular reference to FIGS. 1 and 10-12, the rotatable split or open, ring-like resilient retainer 12 includes the following features: a top discontinuous and substantially planar surface 110; an opposed discontinuous substantially planar bottom surface 112 that runs parallel to the top surface 110; a discontinuous outer cylindrical surface 114 perpendicular to both the top 110 and bottom 112 surfaces; a curved convex transition surface 116 extending between the outer cylindrical surface 114 and the bottom surface 112; a discontinuous inner cylindrical surface 118 spaced from and concentric with the outer cylindrical surface 114; an upper inner frusto-conical surface or bevel 120 extending from the top surface 110 and running inwardly and downwardly toward a central axis C of the retainer 12 and terminating at the inner cylindrical surface 118; and a lower inner frusto-conical surface 122 beginning at a termination of the inner cylindrical surface 118 and extending downwardly and outwardly away from the axis C and terminating at the bottom surface 112. When assembled with the receiver 10, the retainer 12 central axis C is the same as the central axis of rotation B of the receiver 10. When in a neutral state and in an expanded state, the retainer 12 top and bottom surfaces are substantially uniformly planar and parallel. However, as shown in FIG. 13, when the resilient retainer 12 is compressed or contracted during assembly with the receiver 10, portions of the retainer may overlap as will be described in greater detail below. This is possible due to the resiliency and small size of the retainer 12 and a small slit or gap, generally 125 located between opposed end surfaces 127 and 128 of the retainer 12. The surfaces 127 and 128 are slightly spaced from one another, both the surfaces 127 and 128 being substantially perpendicular to the top surface 110. In other embodiments, the surfaces 127 and 128 may not be parallel to one another or both surfaces may be at a similar oblique angle with respect to the top surface 110. It is foreseen that in some embodiments of the invention, the retainer 12 may have more or fewer planar and cylindrical surfaces. In other embodiments, the retainer 12 may be circular in cross-section, e.g., in the form of a split ring or wire. In the illustrated embodiment, the retainer 12 surface geometry results in the inner upper frusto-conical surface 120, or at least a portion or edge thereof being in operative, fixed frictional engagement with the spherical surface 34 of the shank head 8 when the retainer outer cylindrical surface 114 is pressed against the receiver cylindrical surface 98 and the retainer outer curved transition surface 116 is seated against the receiver transition surface 99 with the retainer base surface 112 being seated on the receiver annular surface 100 due to downward pressure of the shank head 8 against the retainer 12 (see, e.g., FIGS. 23-29).

With reference to FIGS. 1 and 22-29, for example, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface of uniform diameter. The illustrated rod 21 is sized for use on the cervical spine and thus has a diameter of 3.5 mm and may have a diameter as small as about 3.0 mm and as large as about 4.0 mm. The rod 21 may be made from a variety of metals, including hard and soft metal alloys and hard and soft or deformable and less compressible plastics, including, but not limited to rods made of elastomeric, polyetheretherketone (PEEK) and other types of materials.

In other embodiments, it is foreseen that longitudinal connecting members for use with the assembly 1 may take a variety of shapes, including but not limited to rods or bars of oval, rectangular or other curved or polygonal cross-section. Some other embodiments may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the receiver 10. The longitudinal connecting member may be integral or otherwise fixed to a bendable or damping component that is sized and shaped to be located between adjacent pairs of bone screw assemblies, for example. A damping component or bumper may be attached to the longitudinal connecting member at one or both sides of the bone screw assembly. A rod or bar (or rod or bar component) of a longitudinal connecting member may be made of a variety of materials ranging from soft deformable plastics to hard metals, depending upon the desired application. Thus, bars and rods may be made of materials including, but not limited to metal and metal alloys including but not limited to stainless steel, titanium, titanium alloys and cobalt chrome alloys; or other suitable materials, including plastic polymers such as polyetheretherketone (PEEK), ultra-high-molecular weight-polyethylene (UH-MWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 22-29, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes an outer helically wound guide and advancement structure 142 in the form of a flange that operably joins with the guide and advancement structure 72 disposed on the arms 62 of the receiver 10. The flange form utilized in accordance with embodiments of the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to control an amount of splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the small size of the cervical screw and longitudinal connecting member. A single start flange form 142 is illustrated; however, it is foreseen the closure 18 may have two starts with cooperating flange form structure on the receiver arms 62. The illustrated closure structure 18 also includes a top surface 144 with an internal drive 146 in the form of an aperture that is illustrated as a hex-shaped internal drive, or may be, for example, a star-shaped or Torx drive, or other internal drives such as slotted, tri-wing, spanner, two or more apertures of various shapes, and the like. A driving tool (not shown) sized and shaped for engagement with the internal drive 146 is used for both rotatable engagement and, if needed, disengagement of the closure 18 from the receiver arms 62. It is also foreseen that in larger embodiments, the closure structure 18 may alternatively include a break-off head designed to allow such a head to break from a base of the closure at a preselected torque. Such a closure structure would also include a base having an internal drive to be used for closure removal. The drive extends all the way through the closure to a bottom surface 148 of the closure and may include a rim in some embodiments. The drive provides a cannulation through bore extending along a central axis thereof and through the top and bottom surfaces thereof. Such a through bore provides a passage through the closure 18 interior for a length of wire (not shown) inserted therein to provide a guide for insertion of the closure top into the receiver arms 62 in some embodiments an methods.

The components of the assembly 1, closure top 18 and the rod 21 may be made from a variety of materials including metals and non-metals, including, but not limited to titanium, titanium alloys, stainless steel, cobalt chrome alloys, polymers such as polyetheretherketone (PEEK) and carbon fiber polymers. For example, the assembly may include a retainer 12 preferably made from titanium, a titanium alloy or a cobalt chrome alloy and the cooperating receiver and shank may also be made from any of those materials. A particularly preferred retainer 12 is made from a cobalt chrome alloy. However, it is noted when the retainer 12 is made from cobalt chrome, a cooperating receiver 10 and shank 4 should not be made from stainless steel.

With reference to FIGS. 13-18, the receiver 10 and retainer 12 are preferably assembled at a factory setting that includes tooling for holding and alignment of the component pieces as well as compressing the retainer 12 prior to insertion into the receiver 10. In some circumstances, the shank 4 is also assembled with the receiver 10 and retainer 12 at the factory. In other instances, it may be more desirable for the surgical staff to pre-assemble a shank of a desired size and/or variety (e.g., surface treatment of roughening the upper portion 8 and/or hydroxyapatite on the shank 6), with the receiver and retainer. Allowing the surgeon to choose the appropriately sized or treated shank 4 advantageously reduces inventory requirements, thus reducing overall cost.

Also, it may be desirable in some instances to implant the shank 4 into a vertebra first, followed by pressing the retainer (that is already captured in the receiver) over the shank. In some instances, this may not be desirable due to the small size of the assembly 1 and the fragile nature of the smaller cervical spine vertebrae for which the assembly 1 is designed.

In addition to being inventory friendly as described above, the assembly 1 components may be provided to the end user in a tracking friendly and sterilization friendly manner. The pre-assembled receiver 10/retainer 12 combination may be sterilized and individually packaged by the vendor, with each pre-assembly package having a discrete tracking number. Likewise, each shank 4 may be individually sterilized, packaged and given a tracking number that may be placed on the package. In other instances, an assembly 1 that includes the shank 4, receiver 10 and retainer 12 combination may be provided to the end user in a sterilized package with a tracking number.

Vendor pre-assembly of the receiver 10 with the open ring retainer 12 is shown in FIG. 13. The retainer 12 is bottom loaded into the receiver 10 through the receiver opening 81. In order to clear the receiver opening at the cylindrical surface 102, the retainer 12 is compressed with the opposed surfaces 127 and 128 that define the gap or slit 125 initially pressed toward one another an then maneuvered until a portion of the retainer base surface 112 overlaps onto the retainer top surface 110 with one of the end surfaces 127 or 128 located generally above the other end surface as shown in phantom in FIG. 13. Due to the small size of the retainer 12, such manipulation of the retainer 12 is possible and the resulting temporarily overlapping retainer is positioned within the receiver cavity 61. Once the retainer 12 is moved passed the cylindrical surface 102, the resilient retainer 12 is released and returns to a neutral or near neutral orientation as shown in solid lines in FIG. 13 with the small gap or slit 125 located between the opposed end surfaces 127 and 128. In both FIGS. 13 and 14, the now captured retainer 12 is blocked from exiting the bottom opening 81 of the receiver by the annular retainer seating surface 100. Now the retainer 12 is ready to be assembled with the shank 4 at the factory or, alternatively, be shipped to an end user as a sub-assembly (shown in FIG. 13); the end user (e.g., surgical staff) will thereafter assemble the combination with a desired shank 4.

Figure 14:
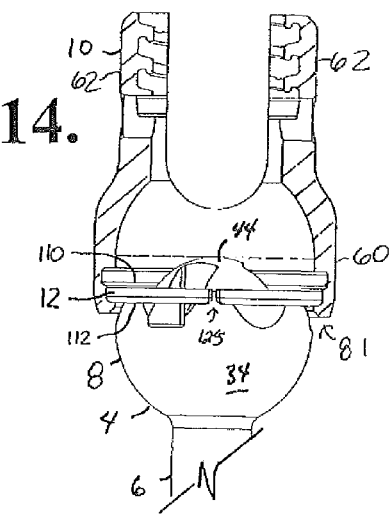
FIG. 14 is a front elevational view with portions broken away of the receiver and retainer of FIG. 13 and also showing the shank if FIG. 1 in an initial approach for assembly with the retainer, the shank being in partial front elevation.

With reference to FIGS. 14-18, the shank 4 is shown in various stages of assembly with the receiver 10 and captured retainer 12. If performed by the surgical staff, such stages may be performed either before or after the shank 4 is implanted into bone. FIGS. 14-18 illustrate a procedure in which the shank 4 is implanted into bone after the shank 4 is connected to the receiver and retainer sub-assembly. As shown in FIG. 14 the shank axis A and the receiver axis B are preferably aligned during assembly, however, exact axial alignment is not required. It is noted that although the retainer 12 is now captured within the receiver 10 such that very little tilt is allowed and thus most movement of the retainer 12 during assembly is axial or up and down movement along the receiver axis B, the retainer 12 may also be rotated with respect to the receiver 10 about the receiver axis B. With further reference to FIG. 14, the shank 4 is initially positioned beneath the receiver bottom surface 80 at the opening 81 and also beneath the retainer bottom surface 112 with the shank head 8 domed surface 44 initially moved up and through the retainer inner surfaces 122 and 118. With further reference to FIG. 15, as the shank head spherical surface 34 abuts against the retainer inner frusto-conical surface 122, the shank head 8 pushes the retainer 12 top surface 110 into abutment with the receiver ceiling surface 92. With reference to FIG. 16, as the shank head 8 continues to move upwardly toward the receiver arm u-shaped channel 62, the resilient ring retainer 12 cannot move upwardly and thus expands outwardly into the expansion chamber defined by the receiver surfaces 92, 94 and 96. Continued upward movement of the shank head surface 34 causes the surface 34 to slide first along the frusto-conical surface 122 and then the inner cylindrical surface 118 of the retainer 12, the gap 125 widening until the retainer outer cylindrical surface 114 abuts against the receive cylindrical surface 94 and the hemisphere H1 moves through and past the retainer ring 12. FIG. 16 shows the maximum expansion of the ring 12 and FIG. 17 shows a resilient return of the retainer 12 to a neutral or near neutral state after the shank hemisphere H1 passes through the retainer 12. FIG. 17 also shows how the retainer ring 12 then drops down to the retainer seat 100. In some embodiments, the shank 4 and the receiver 10 may need to be pulled in opposite directions away from one another to result in a fully seated retainer ring 12 as shown in FIG. 18. At this time, the shank head 8 is captured within the receiver 10, and as is shown in FIG. 18, the spherical surface 34 may be placed into engagement with the retainer 12 at the inner surface 120. The spherical surfaces 34 and 44 of the shank are not in engagement with any of the inner surfaces of the receiver 10. Only the retainer ring 12 is engagement with the receiver, but remains rotatable about the receiver axis B. At this time, the shank 4 is freely pivotable (side to side, forward to back and all pivoting movements therebetween) and rotatable with respect to the retainer 12 and thus also with respect to the receiver 10.

With reference to FIGS. 19-21, the fully assembled bone anchor assembly 1 made up of the connected shank 4, retainer 12 and receiver 10 are shown with the driver 24 for implanting the bone anchor shank 4 into the vertebra 17. As shown in FIG. 19, the driver 24 is received through the top opening 66 of the receiver and, as shown in FIGS. 20 and 21 is lowered until the three prongs 57 are fully seated in the shank three-slotted drive 42 with the driver prong base surfaces 58 abutting against the internal drive seating surfaces 50. The driver shaft 59 is then rotated until the bone screw shank 6 is implanted to a desired location in the vertebra 17. Then the driver 24 is removed out of the top opening 66 of the receiver 10.

In some procedures, the vertebra 17 may be pre-drilled to minimize stressing the bone and have a guide wire (not shown) inserted therein to provide a guide for the placement and angle of the shank 4 (in embodiments wherein the shank is cannulated) with respect to the vertebra. A further tap hole may be made using a tap with the guide wire as a guide. Then, the assembly 1 may be threaded onto the guide wire utilizing the cannulation bore. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. As indicated earlier, if desired, the shank 4 alone may be driven into the vertebra 17 utilizing the pronged driver 24 without the remainder of the assembly 1, followed by pressing the receiver 10 and captured open retainer 12 onto the shank head 8. In such embodiments, the shank 4 may either be driven to a desired final location or may be driven to a location slightly above or proud to provide for ease in assembly with the pre-assembled receiver 10 and retainer 12. Thereafter, the shank 4 may be driven deeper into the vertebra 17 as illustrated in FIGS. 19-21 and previously described herein.

At this time and with reference to FIGS. 23-29, the receiver 10 may be articulated to a variety of angular positions with respect to the shank 4 prior to insertion of the rod 21 or closure top 18. Also with reference to FIGS. 22-29, the rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 146 until a selected pressure is reached (typically about 40-50 inch pounds of torque) at which point the rod 21 frictionally engages and fixes against the domed surface 44 of shank head 8. The rod 21 pressing down on the surface 44 also urges the shank upper portion 8 spherical surface 34 toward the retainer inner surface 120 or outer edge thereof and into locking engagement therewith, the retainer 12 frictionally abutting and expanding outwardly against the receiver 10 at one or more of the surfaces 98, 99 and 100.

FIG. 22 shows the assembly 1 in a locked position with the rod 21 and closure top 18 wherein the shank 4 axis A is substantially aligned with receiver axis B. FIGS. 23 and 24 show the assembly 1 in an alternative locked position with the rod 21 and the closure top 18 wherein the receiver 10 had been previously pivoted with respect to the shank 4 to a forty-four degree angle with the rod 21 being substantially received in one of the concave surface cut-outs 40 formed in the spherical surface 34 to allow for such extended pivot of the shank with respect to the receiver (shown in the sagittal plane and with the shank directed caudally). FIGS. 25 and 26 illustrate the same assembly in an opposite forty-four degree angulation of the receiver with respect to the shank in a sagittal plane/cephalic direction. In such angulation, the rod 21 is also substantially received on one of the concave surface features 40 that includes a drive slot 48. However, as shown in FIG. 26, the rod 21 is adequately supported by remaining portions of the feature 40 and does not extend into the drive slot 48. Furthermore in both the cephalic and caudally directed extended angles, the spherical surface portions 34 located between the carved out features 40 are adequate to securely hold the shank head 8 in a fixed position against the retainer 12. With reference to FIG. 27, the receiver 10 has been pivoted with respect to the shank 4 (prior to locking of the closure 18 onto the rod 21) to a forty-four degree angle in the transverse plane. Finally, with reference to FIGS. 28 and 29, a twenty-four degree angulation between the shank 4 and the receiver 10 is shown along with rotation of the shank, showing how the rod may in some instances be fixed in position against the dome 44 and the edge 36 of the spherical surface 34.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly for surgical implantation, the assembly comprising: a receiver having a base and opposed arms, the base having an inner cavity and the arms forming a longitudinal connecting member receiving channel, the channel communicating with the inner cavity; a shank having a threaded body and a head, the threaded body for implantation into bone and the head being captured within the inner cavity, the shank being pivotable with respect to the receiver; and a separate retaining structure located within the inner cavity that retains the shank head within the receiver, wherein:
   a) the inner cavity is partially defined by a lower seat and partially defined by a retaining structure expansion chamber located above the lower seat, the lower seat sized and shaped for operatively frictionally holding the retaining structure;
   b) the retaining structure being open and resilient, the shank head being bottom-loadable into the receiver, the retaining structure expandable about the head in the expansion chamber during loading of the head into the receiver; and
   c) the shank head having a first convex surface with a first radius that is sized and shaped for direct contact with a longitudinal connecting member to receive direct downward force from direct engagement with the longitudinal connecting member, the shank having a second lower convex surface having a second radius that is larger than the first radius, the second lower convex surface being operationally spaced from the receiver and in direct engagement with the retaining structure and fixed thereto when the longitudinal connecting member places direct downward force on the first convex surface, the second lower convex surface terminating at an upper perimetric edge and wherein one and up to a plurality of concave surface features are formed into the second lower convex surface at and near the upper perimetric edge, each concave surface feature sized and shaped for receiving a portion of the longitudinal connecting member to allow for an increased angle of pivot between the shank and the receiver, the upper perimetric edge being made discontinuous by the one and up to plurality of concave surface features.

2. The polyaxial bone screw assembly of claim 1 wherein the second lower convex surface is substantially spherical and has a hemisphere, the upper perimetric edge located above the hemisphere.

3. The polyaxial bone screw assembly of claim 1 wherein the upper perimetric edge forms a discontinuous circle.

4. The polyaxial bone screw assembly of claim 1 wherein both the first convex surface and the second lower convex surface are substantially spherical.

5. The polyaxial bone screw assembly of claim 1 wherein the first convex surface has an internal drive formed thereon.

6. The polyaxial bone screw assembly of claim 1 wherein an internal drive slot is formed in the one and up to a plurality of concave surface features.

7. The polyaxial bone screw assembly of claim 1 wherein the open retaining structure is up-loadable into the inner cavity.

8. The polyaxial bone screw assembly of claim 7 wherein the retaining structure includes surfaces that overlap during uploading into the inner cavity.

9. A polyaxial spinal bone screw assembly for receiving and fixing placement of a longitudinal connecting member, the assembly comprising:
   a) a bone screw shank having a body integral with a shank upper structure, the shank upper structure having a top first surface that is convex spherically shaped and having a first radius, a lower second surface that is convex partially spherically shaped and having a second radius, a third annular surface extending outwardly from the top first surface and terminating at the lower second surface and one and up to a plurality of concave surface features formed in the lower second and the annular third surfaces;
b) a receiver having a pair of arms forming a channel, the receiver also having a cavity with a concave partially spherically shaped surface adapted to allow pivotal movement of the top first and the lower second surfaces of the shank during positioning and a lower opening to an exterior of the receiver opposite the pair of arms, the cavity communicating with the channel, the cavity further defined by a lower seat and an expansion area located above the lower seat, the shank upper structure being uploaded and received in the cavity through the lower opening;
c) an open and resilient ring-like retainer receivable in the cavity and outwardly biased against the receiver in fixed relation thereto at the lower seat of the receiver when the shank upper structure is in the receiver, the retainer expanding about the shank upper structure when the shank upper structure is loaded into the receiver through the lower opening and having a retainer surface sized and shaped to operationally frictionally engage the lower second surface of the shank and retain the shank upper structure within the cavity, the shank upper structure sized and shaped to extend above the retainer with the top first surface of the shank receiving direct downward force from contact with the longitudinal connecting member so as to lock an angular position of the receiver relative to the shank, the assembly having an unlocked position wherein the shank upper structure is in sliding, pivotable relation with the retainer and a locked position wherein the lower second surface is in fixed frictional engagement with the retainer surface; and wherein
d) when in an unlocked position a portion of the rod may be received in an area defined by one of the one and up to a plurality of concave surface features to provide an increased angle of articulation between the shank and the receiver and another portion of the rod may then be fixed into locking engagement with the top first convex surface of the shank.

10. The polyaxial spinal bone screw assembly of claim 9 wherein the top first convex surface has an internal drive formed thereon.

11. The polyaxial spinal bone screw assembly of claim 9 wherein an internal drive slot is formed in one and up to a plurality of the concave surface features.

12. The polyaxial spinal bone screw assembly of claim 9 wherein the retainer is up-loadable into the cavity.

13. A polyaxial bone anchor, the improvement comprising
a) a receiver defining a chamber communicating with a channel, the channel sized and shaped for receiving a portion of a longitudinal connecting member, the chamber defined in part by a lower seat and in part by an expansion area located between the lower seat and the channel;
b) a shank having a shank upper portion with a first surface and a second surface, the first and second surfaces being convex partially spherical shaped, and a plurality of spaced concave surface features formed in the second surface, each concave surface feature defining an area for receiving a portion of the longitudinal connecting member, the second surface being larger than the first surface, the first surface configured for direct frictional engagement with the longitudinal connecting member, the second surface having a hemisphere and terminating at a spheric edge located above the hemisphere, the spheric edge being located below the first surface, the spaced concave surface features located about and running through the spheric edge; and
c) an open retainer located in the chamber, the retainer expandable in the chamber about the shank upper portion at the expansion area and receiving the upper portion therethrough to capture the upper portion in the chamber, the retainer being in an expanded state and fixed between the second surface of the shank upper portion and the lower seat of the receiver when the shank is in a frictionally fixed orientation with respect to the receiver.

* * * * *